United States Patent [19]
Horst

[11] Patent Number: 6,103,763
[45] Date of Patent: *Aug. 15, 2000

[54] METHODS OF KILLING INSECTS

[75] Inventor: R. Kenneth Horst, Ithaca, N.Y.

[73] Assignee: H & I Agritech, Inc., Ithaca, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/625,527

[22] Filed: Mar. 28, 1996

Related U.S. Application Data

[60] Provisional application No. 60/013,714, Mar. 20, 1996.

[51] Int. Cl.⁷ .......................... A01N 37/04; A01N 33/18; A01N 41/04; A01N 25/06
[52] U.S. Cl. .......................... 514/547; 514/552; 514/711; 514/741; 424/84; 424/405; 424/663
[58] Field of Search .......................... 514/547, 552, 514/711, 741, 937, 944, 945; 424/84, 405, 663, 43

[56] References Cited

U.S. PATENT DOCUMENTS

| | | | |
|---|---|---|---|
| 4,307,115 | 12/1981 | Klopping | 514/477 |
| 4,318,920 | 3/1982 | Stein | 514/523 |
| 4,374,853 | 2/1983 | Workman | 514/506 |
| 4,731,379 | 3/1988 | Panzer | 514/547 |
| 4,889,710 | 12/1989 | Hagarty | 424/84 |
| 4,945,107 | 7/1990 | Minetti | 514/473 |
| 4,997,592 | 3/1991 | Woogerd | 71/DIG. 1 |
| 5,489,433 | 2/1996 | Aboud | 424/405 |
| 5,610,186 | 3/1997 | Workman | 514/547 |
| 5,882,669 | 3/1999 | Hondo et al. | 424/408 |

FOREIGN PATENT DOCUMENTS

| | | |
|---|---|---|
| 322583 | 7/1989 | European Pat. Off. . |
| 4069302 | 3/1992 | Japan . |
| 2016443 | 11/1990 | Spain . |

OTHER PUBLICATIONS

Derwent Abstract, Accession No. 90–356595 (1990).
King, W.V., Chemicals Evaluated as insecticides and repellents at Orlando, FLA., Agricultural Handbook No. 69, USDA, May 1954, pp. 5–7 and 318.
Chemical Abstracts 117:145360 (1992).

*Primary Examiner*—John Pak
*Attorney, Agent, or Firm*—Brown, Pinnis & Michaels, P.C.

[57] ABSTRACT

An environmentally safe method of killing insects and arachnids is disclosed herein. Insects and arachnids can be killed by the direct application of a solution of surfactant comprising between 0.01% and 10% of an alkali metal or ammonium salt of $C_6$ to $C_{14}$ dialkyl sulfosuccinate. The alkali metal or ammonium salt of $C_6$ to $C_{14}$ dialkyl sulfosuccinate can be applied with attractants to surfaces near or at surfaces where the elimination of arachnids or insects is needed.

11 Claims, No Drawings

METHODS OF KILLING INSECTS

REFERENCE TO RELATED APPLICATIONS

Priority is claimed under 35 U.S.C. §119 for a provisional application Ser. No. 60/013,714 filed Mar. 2, 1996 entitled "METHODS OF KILLING INSECTS".

FIELD OF THE INVENTION

The invention pertains to the field of insecticides. More particularly, the invention pertains to the new use of environmentally safe compounds to kill insects.

BACKGROUND OF THE INVENTION

Insects and arachnids can have serious negative effects on the quality of human life. Firstly, when found in the home such pests can be a source of annoyance purely due to their presence and they can also spread disease. Secondly, on plants and crops these pests can destroy foliage and adversely affect plant growth reducing yields of crops and their quality. They can decrease the aesthetic value of ornamental plants.

A broad range of organic molecules have been found to be toxic to insects and arachnids and are used for their control. However, with such molecules there is significant concern of damage to the environment and adverse effects on humans. Several of the compounds used in insect control are only slowly biodegraded or are non-biodegradable, In many cases insects develop immunity to the use of some types of insecticides making them useless for long term use.

Therefore there is a real need to provide insecticides which are safe in the environment and non-toxic to humans and animals, which are rapidly biodegradable and to which insects do not become immune after long term use.

While surfactants have long been used as adjuvants for other pesticides, they are not generally known to provide insecticidal activity of their own. Thus surfactants are often used as spreader stickers to enhance the activity of fungicides. For example, U.S. Pat. No. 5,468,716 (Winston) describes the use of sulfosuccinate surfactants in combination with other anionic surfactants to promote the activity of bicarbonates in controlling fungi on plants. However, there is no suggestion that such materials will be effective in controlling insects.

SUMMARY OF THE INVENTION

The present invention provides a plant, animal, human and environmentally safe method of killing insects and arachnids. Direct application of a solution of certain safe surfactants has been found to rapidly kill several types of insects and arachnids. Products of the invention are safe and effective for eradicating insects and arachnids for home use as well as on plants and crops.

One method of the present invention teaches killing insects and arachnids by the direct application of a solution of surfactant comprising between 0.01% and 10% of an alkali metal or ammonium salt of $C_6$ to $C_{14}$ dialkyl sulfosuccinate.

Another method of the present invention teaches killing insects and arachnids by applying a combination of alkali metal or ammonium salt of $C_6$ to $C_{14}$ dialkyl sulfosuccinate with attractants to surfaces near or at surfaces where the elimination of arachnids or insects is needed.

DETAILED DESCRIPTION

The present invention provides a plant, animal, human and environmentally safe method of killing insects and arachnids, specifically by direct application of a solution of including a surfactant comprising between 0.01% and 10% of an alkali metal or ammonium salt of $C_6$ to $C_{14}$ dialkyl sulfosuccinate.

The present invention was discovered while testing a formulation for a different purpose that included potassium bicarbonate (85%), sodium lauryl sulfate (5.025%) and sodium dioctyl sulfosuccinate (9.975%). It was noticed that this formulation tended to have some insecticidal activity. A series of experiments were designed to test each compound in the formulation to determine which was responsible for the insecticidal properties.

The compounds were first tested on aphids. An untreated barley leaf was placed in a container with a piece of filter paper. Five adult aphids were placed in each container and left overnight to allow the aphids to attach to the leaves and begin feeding. The next day the containers were sprayed with a treatment of compound and water at the following concentrations.

| Compound | Concentration | Results |
| --- | --- | --- |
| sodium lauryl sulfate (SLS) | 0.0295% | immediately killed the nymphs and delayed death to some adults |
| sodium dioctyl sulfosuccinate (Geropon SDS ™) | 0.0587% | immediate kill of all insects |
| sodium lauryl sulfate & sodium dioctyl sulfosuccinate | same as above | immediate kill of all insects |
| potassium, bicarbonate | 0.4998% | no affect |
| water | — | no affect |

From these experiments it is was determined that the sodium dioctyl sulfosuccinate was the primary compound responsible for the insecticidal activity. Sodium dioctyl sulfosuccinate is used in the pharmaceutical, industrial, cosmetic and food industry. It is primarily used as a surfactant or wetting agent, but is also used as an adjuvant in tablet formulation or as a dispersing and solubilizing agent in foods. It is sold under a number of trademarks, specifically Geropon SDS™, sold by Rhone-Poulenc and Aerosol OT-B, sold by Cytec Industries were tested for efficacy. Prior to the present invention it was unknown that this compound had any insecticidal activity. A series of experiments were designed to determine the effective dose range. The following concentrations were tested.

| Compound | Concentration | Results |
| --- | --- | --- |
| sodium dioctyl sulfosuccinate (Geropon SDS ™) | 0.147 mg/ml | immediate kill of all insects |
| sodium dioctyl sulfosuccinate (Geropon SDS ™) | 0.0733 mg/ml | immediate kill of all nymphs and 70% of adults |
| sodium dioctyl sulfosuccinate (Geropon SDS ™) | 0.0367 mg/ml | immediate kill of most nymphs, but no adults |
| sodium dioctyl sulfosuccinate (Aerosol OT-B ™) | 0.147 mg/ml | immediate kill of all insects |
| sodium dioctyl sulfosuccinate (Aerosol OT-B ™) | 0.0733 mg/ml | immediate kill of all nymphs and 80% of adults |

-continued

| Compound | Concentration | Results |
|---|---|---|
| sodium dioctyl sulfosuccinate (Aerosol OT-B ™) | 0.0367 mg/ml | immediate kill of most nymphs, but only 20% of adults |
| sodium dioctyl sulfosuccinate (Aerosol OT-B ™) | 0.0183 mg/ml | immediate kill of some nymphs, but no adults |
| water | — | no affect |

In general, it was noted the effective dose was between 0.0733 and 0.147 mg/ml. The Aerosol OT-B™ took slightly less time than Geropon SDS™ to kill insects and worked better at lower concentrations. The damage to the insects appears to be complete within 5 minutes of contact; no change was observed at 30 minutes, 1 hour or 3 hours after contact.

Sodium dioctyl sulfosuccinate (Geropon SDS™) was also tested for activity against German cockroaches, Blattella (supplied by Carolina Biological Supply) and were maintained in clean holding cages. The cockroaches (10–20) were transferred to small plastic boxes covered by cheese-cloth and sprayed through the cheese-cloth cover from a distance of 1 foot with a water control and a sodium dioctyl sulfosuccinate (Geropon SDS™) treatment at 1.18 mg/ml concentration. The cockroaches were exposed to the treatments for 15 minutes after the propellants evaporated and then transferred to clean holding cages. Within 30 seconds after spraying with the sodium dioctyl sulfosuccinate treatment all 20 cockroaches were dead. All of the cockroaches sprayed with water survived for over a week until the experiment was discontinued.

Thus a plant, animal, human and environmentally safe method of killing insects and arachnids was discovered. The present invention teaches that direct application of a solution of including a surfactant comprising between 0.01% and 10% of an alkali metal or ammonium salt of $C_6$ to $C_{14}$ dialkyl sulfosuccinate is effective. Such surfactants are known in the art, but have not been used for this purpose previous to the work of the present inventors. Preferred sulfosuccinate salts are those with alkyl chain lengths of between $C_8$ and $Cl_2$. Preferably the solution medium is water. However, non-aqueous mediums would also be effective.

When used in direct application against insects and arachnids concentrations between 0.015 to 10% are utilized. For insects in most cases the preferred concentrations of the surfactant are between 0.1 to 1% Such concentrations are highly effective against insects such as cockroaches and aphids while at the same time being benign to humans and animals and have been found not to be phytotoxic to most plants When applying to insects on turf grasses, concentrations in the range 0.02%–0.1% are preferred for efficacy While preventing phytotoxicity. For arachnids somewhat higher doses may be needed.

The product can be provided as a dry mix which is dissolved in water before application, as a concentrate which is diluted in water before use or as a ready to use solution which is sprayed directly onto the pests being controlled.

When used with attractants the sulfosuccinate may be used in concentrations of up to about 50%. Suitable attractants include various sugars, corn starch or other edible materials which might attract the pests to be killed. This product can be provided as a dry mix which is applied in dry form, as a concentrate which is diluted in water before use or as a ready to use solution which is sprayed onto surfaces being treated where pest control is needed.

In addition to the dialkyl sulfosuccinate of the invention other ingredients may be added to the formulation such as additional insecticidal ingredients which provide longer lasting residual action.

Advantages of the formulations of the invention are safety to humans and animals. The materials are very rapidly biodegraded and are therefore environmentally benign. They are not phytotoxic to most plants. They are extremely quick in their ability to kill. It has been noted with cockroaches and aphids that death can occur within 20 seconds of contact with the spray. Based on the rapidity with which kill is achieved it is believed that development of immunity by insects and arachnids is unlikely.

From these preliminary studies various formulations were developed. The following provides examples of formulations of the invention.

EXAMPLE I

The following product is a ready to use insecticide and arachnicide for household use.

| | |
|---|---|
| Sodium dioctyl sulfosuccinate | 1.0% |
| Water | 99.0% |

The product is applied directly from a hand spray pump container. When sprayed directly at cockroaches or aphids, death results in 20–30 seconds. No phytotoxicity is noted when this product is applied to roses,

EXAMPLE II

| | |
|---|---|
| Sodium didecyl sulfosuccinate | 0.2% |
| Pentachloronitrobenzene | 0.01% |
| Water | 99.79% |

The product is applied to plants infested with aphids and mites. Residual PCNB provides protection against fungal attack, Inspection of the plants 24 hours later shows the lack of live aphids and mites.

EXAMPLE III

| | |
|---|---|
| Potassium didodecyl sulfosuccinate | 10.0% |
| Sodium chloride | 90.0% |

The product is dissolved at a ratio of 1 part product to 500 parts water and sprayed directly onto household pests such as cockroaches, ants, or spiders. Death of insects results in 20 seconds. Death of spiders may take longer.

EXAMPLE IV

| | |
|---|---|
| Sodium dinonyl sulfosuccinate | 50.0% |
| Glucose powder | 25.0% |
| Corn starch | 25.0% |

The product is dissolved as a 1% solution in water and sprayed liberally on surfaces near sources of cockroaches or into their nests. Rapid control is achieved.

EXAMPLE V

| | |
|---|---|
| Sodium dicotyl sulfosuccinate | 10.0% |
| Granular sugar | 90.0% |

The product is applied as granules in area where control is needed. Two days after application the product and dead insects are removed by vacuum.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of killing insects, comprising: applying a surfactant composition comprising a salt of $C_7$ and $C_9$ to $C_{14}$ dialkyl sulfosuccinate so that said dialkyl sulfosuccinate salt comes into contact with said insects to be killed, wherein said dialkyl sulfosuccinate salt is the only insecticidal agent present in said surfactant composition and wherein the concentration of said dialkyl sulfosuccinate salt is between 0.01% and 10% by weight and wherein said dialkyl sulfosuccinate salt is selected from the group consisting of:
   a) sodium didecyl sulfosuccinate;
   b) potassium didodecyl sulfosuccinate;
   c) sodium dinonyl sulfosuccinate;
   d) sodium diundecyl sulfosuccinate;
   e) sodium diheptyl sulfosuccinate;
   f) sodium ditridecyl sulfosuccinate; and
   g) sodium ditetradecyl sulfosuccinate.

2. The method of claim 1 wherein said surfactant is provided in an aqueous solution.

3. The method of claim 1 wherein said surfactant is applied in combination with at least one fungicidal compound.

4. The method of claim 1 wherein an effective amount of the surfactant composition of claim 1 is administered in conjunction with the administration of a hormonal or sensory attractant for natural predators of the insects to be killed or eliminated.

5. The method of claim 1 wherein said insects to be killed are selected from the group consisting of:
   a) aphids;
   b) cockroaches; and
   c) ants.

6. The method of claim 1 wherein said dialkyl sulfosuccinate salt is applied in an aerosol form so that said compound will come into contact with said insects to be killed, wherein said dialkyl sulfosuccinate salt is at least, 2% by weight, of the total composition applied.

7. The method of claim 1 wherein sodium chloride comprises at most 90% of the dry weight of said surfactant composition and said dialkyl sulfosuccinate salt is potassium didodecyl sulfosuccinate.

8. The method of claim 1 wherein said dialkyl sulfosuccinate salt is sodium dinonyl sulfosuccinate.

9. The method of claim 3 wherein said at least one fungicidal compound is pentachloronitrobenzene.

10. The method of claim 9 wherein said dialkyl sulfosuccinate salt is sodium didecyl sulfosuccinate.

11. A method of killing arachnids, comprising: applying a surfactant composition comprising a $C_7$ and $C_9$ to $C_{14}$ dialkyl sulfosuccinate salt so that said salt will come into contact with said arachnids to be killed, wherein said dialkyl sulfosuccinate salt is the only pesticidal agent present in said surfactant composition, wherein said surfactant composition is applied in an aerosol form, and wherein the concentration of said salt in said surfactant composition is between 0.01% and 10% by weigh and wherein said dialkyl sulfosuccinate salt is selected from the group consisting of:
   a) sodium didecyl sulfosuccinate;
   b) potassium didodecyl sulfosuccinate;
   c) sodium dinonyl sulfosuccinate;
   d) sodium diundecyl sulfosuccinate;
   e) sodium diheptyl sulfosuccinate;
   f) sodium ditridecyl sulfosuccinate;
   g) sodium ditetradecyl sulfosuccinate.

* * * * *